United States Patent
Liu et al.

(10) Patent No.: US 11,896,312 B2
(45) Date of Patent: Feb. 13, 2024

(54) IMAGE-GUIDED LUNG TUMOR PLANNING AND ABLATION SYSTEM

(71) Applicant: BRONCUS MEDICAL INC., San Jose, CA (US)

(72) Inventors: Yixun Liu, San Jose, CA (US); Ronnarit Cheirsilp, San Jose, CA (US); Kun-Chang Yu, San Jose, CA (US); Henky Wibowo, San Jose, CA (US)

(73) Assignee: BRONCUS MEDICAL INC., San Jose, CA (US)

( * ) Notice: Subject to any disclaimer, the term of this patent is extended or adjusted under 35 U.S.C. 154(b) by 832 days.

(21) Appl. No.: 16/963,745

(22) PCT Filed: Feb. 4, 2019

(86) PCT No.: PCT/US2019/016529
§ 371 (c)(1),
(2) Date: Jul. 21, 2020

(87) PCT Pub. No.: WO2019/152935
PCT Pub. Date: Aug. 8, 2019

(65) Prior Publication Data
US 2021/0401502 A1 Dec. 30, 2021

Related U.S. Application Data

(60) Provisional application No. 62/626,533, filed on Feb. 5, 2018.

(51) Int. Cl.
*A61B 34/10* (2016.01)
*A61B 18/08* (2006.01)
(Continued)

(52) U.S. Cl.
CPC ............ *A61B 34/10* (2016.02); *A61B 18/082* (2013.01); *A61B 18/1492* (2013.01);
(Continued)

(58) Field of Classification Search
CPC .............. A61B 18/082; A61B 18/1492; A61B 2018/00541; A61B 2018/00577;
(Continued)

(56) References Cited

U.S. PATENT DOCUMENTS 7,756,563 B2   7/2010  Higgins et al.
7,889,905 B2   2/2011  Higgins et al.
(Continued)

FOREIGN PATENT DOCUMENTS

DE   102007046453 A1   4/2009
EP       3127485 A1    2/2017

OTHER PUBLICATIONS

EP 19747218.6 Extended Search Report, dated Sep. 30, 2021.
(Continued)

*Primary Examiner* — Khadijeh A Vahdat
(74) *Attorney, Agent, or Firm* — Batt IP A Law Corporation; Richard Batt

(57) ABSTRACT

A lung tumor ablation planning system includes a processor operable to compute a target ablation zone and a set of optimum ablation parameters to create the target lesion with the ablation catheter. A predictive algorithm is employed to model the ablation zone based on training data. Various ablation plans are displayed to the physician corresponding to various metrics including without limitation maximizing tumor ablation coverage, shortest travel, obstacle avoidance, and shortest ablation time. Related methods are described.

24 Claims, 12 Drawing Sheets

(51) Int. Cl.
*A61B 18/14* (2006.01)
*A61B 18/00* (2006.01)

(52) U.S. Cl.
CPC ............... *A61B 2018/00541* (2013.01); *A61B 2018/00577* (2013.01); *A61B 2034/104* (2016.02)

(58) Field of Classification Search
CPC ........ A61B 2034/104; A61B 2034/105; A61B 2034/107; A61B 34/10; A61B 34/25; A61B 2090/376
See application file for complete search history.

(56) References Cited

U.S. PATENT DOCUMENTS

| | | | |
|---|---|---|---|
| 8,709,034 B2 | 4/2014 | Keast et al. | |
| 9,037,215 B2 | 5/2015 | Higgins et al. | |
| 9,265,468 B2 | 2/2016 | Rai et al. | |
| 9,672,631 B2 | 6/2017 | Higgins et al. | |
| 9,875,544 B2 | 1/2018 | Rai et al. | |
| 9,886,760 B2 | 2/2018 | Liu et al. | |
| 2007/0118101 A1* | 5/2007 | Mahesh ................ | G16H 50/50 606/32 |
| 2012/0123400 A1 | 5/2012 | Francischelli et al. | |
| 2012/0289776 A1* | 11/2012 | Keast ................ | A61B 17/0293 600/114 |
| 2014/0022250 A1 | 1/2014 | Mansi et al. | |
| 2014/0128884 A1 | 5/2014 | Altrogge et al. | |
| 2014/0201669 A1 | 7/2014 | Liu et al. | |
| 2017/0156685 A1 | 6/2017 | Dickhans et al. | |
| 2017/0215951 A1 | 8/2017 | Wang et al. | |

OTHER PUBLICATIONS

PCT International Search Report and International Preliminary Report on Patentability for PCT/US2019/016529, dated Jun. 24, 2019.

* cited by examiner

FIG. 12

| RFA PATH | | | | |
|---|---|---|---|---|
| | RFA 1 | RFA 2 | RFA 3 | RFA 4 |
| Airway diameter at POE | 5.2-7.8mm | 5.2-7.8mm | 5.2-7.8mm | 5.2-7.8mm |
| Tunnel length | 44.5mm | 44.5mm | 44.5mm | 44.5mm |
| Distance from POE to vessels | 3.2mm | 3.2mm | 3.2mm | 3.2mm |
| Distance from target to pleura | 10.2mm | 10.2mm | 10.2mm | 10.2mm |
| # of branches traversed | 5 | 5 | 5 | 5 |
| Debug info | RM=0, BS=0.61, CO=0.41, TT=8.00, EX=12.21, EY=12.21, EZ=23.11, ATT=0.42, ATAR=0.96, FX=1, PL=5.00. | RM=0, BS=0.61, CO=0.41, TT=8.00, EX=12.21, EY=12.21, EZ=23.11, ATT=0.42, ATAR=0.96, FX=1, PL=5.00. | RM=0, BS=0.61, CO=0.41, TT=8.00, EX=12.21, EY=12.21, EZ=23.11, ATT=0.42, ATAR=0.96, FX=1, PL=5.00. | RM=0, BS=0.61, CO=0.41, TT=8.00, EX=12.21, EY=12.21, EZ=23.11, ATT=0.42, ATAR=0.96, FX=1, PL=5.00. |
| | ⊘ SELECTED PATH | ○ SELECTED PATH | ○ SELECTED PATH | ○ SELECTED PATH |

Select path ○ Patient: 45-01-01 #45-01-01, CT 1/23/2018 5:35:04 PM  target 1: T1

RFA profile: Default parameters ◆ Go

IMAGE-GUIDED LUNG TUMOR PLANNING AND ABLATION SYSTEM

CROSS-REFERENCE TO RELATED APPLICATIONS

This application claims the benefit of U.S. Provisional Application No. 62/626,533 filed Feb. 5, 2018, the entire contents of which are incorporated herein by reference in their entirety for all purposes.

BACKGROUND

1. Field of the Invention

The present invention relates to methods of treatment planning using minimally invasive surgical devices operable to deliver energy of sufficient intensity to cause targeted ablation of tissue located within a human or animal body.

2. Description of the Related Art

Lung cancer is now the leading cause of cancer death in both men and women in the United States. Of patients with biopsy-proven cancer, only ~30% of patients are surgical candidates due to co-morbid disease, cardiopulmonary function, or advanced age. These patients are typically treated with chemotherapy or ionizing radiation therapy (e.g. stereotactic body radiation therapy, SBRT).

Image-guided lung biopsy with flexible bronchoscopy is an emerging approach that may substantially reduce pneumothorax risk, compared to conventional transthoracic approach. Percutaneous thermal ablation has emerged as a prominent alternate treatment option, with radiofrequency ablation (RFA) being the most widely used energy modality compared to SBRT. RFA has the advantage of employing non-ionizing radiation, thereby being amenable to repeated procedures, offers improved preservation of lung function; and can be delivered at a considerably lower cost. A recent prospective, multi-center study demonstrated the 2-year overall survival rate for thermal ablation to be similar to that of SBRT.

Currently available devices for tumor ablation are limited to a percutaneous approach, such as the Leveen™ Needle Electrode manufactured by Boston Scientific Inc. (Natick, Massachusetts). Generally speaking, use of rigid needles through the skin and pleural membrane come with a high risk of pneumothorax and precludes treatment of central tumors.

Furthermore, there are limited treatment guidance and planning tools placing a large burden on the physician to comparatively assess device insertion paths.

Accordingly, there is still a need to address the above mentioned challenges associated with ablation systems.

SUMMARY OF THE INVENTION

A bronchoscopic-based method for assisting a physician plan a tumor ablation using an ablation applicator includes the steps of receiving image data of the lung of the patient including the target tissue to be ablated, computing, on a processor, an ablation zone and a set of optimum candidate ablation parameters to maximize tumor ablation coverage.

In embodiments of the invention, a lung tumor ablation planning system includes a flexible radio frequency ablation (RFA) applicator that can be delivered via a bronchoscopic approach to the target; a regression modeling engine to predict a tumor ablation zone and generator parameters given a target tumor; and a path planning engine to find the optimal path to deliver the RFA applicator. In embodiments, the system is integrated with guidance systems to assist the physician navigate the RFA device to the target.

In embodiments of the invention, the system operates with a bronchoscope and provides precise and localized ablation of early-stage lung disease.

In embodiments of the invention, a planning and ablation method is integrated with a guided bronchoscopic biopsy technique to facilitate treatment of localized nodules, immediately following positive biopsy, while minimizing the risk of pneumothorax.

In embodiments of the invention, the energy delivery device is integrated with a personalized treatment planning system, allowing physicians to prospectively plan and optimize treatment delivery for patient-specific anatomy.

These advantages as well as other objects and advantages of the present invention will become apparent from the detailed description to follow, together with the accompanying drawings.

BRIEF DESCRIPTION OF THE DRAWINGS

FIG. 12 is an illustration of various ablation planning results for different routes to the target.

DETAILED DESCRIPTION

Figure 1:
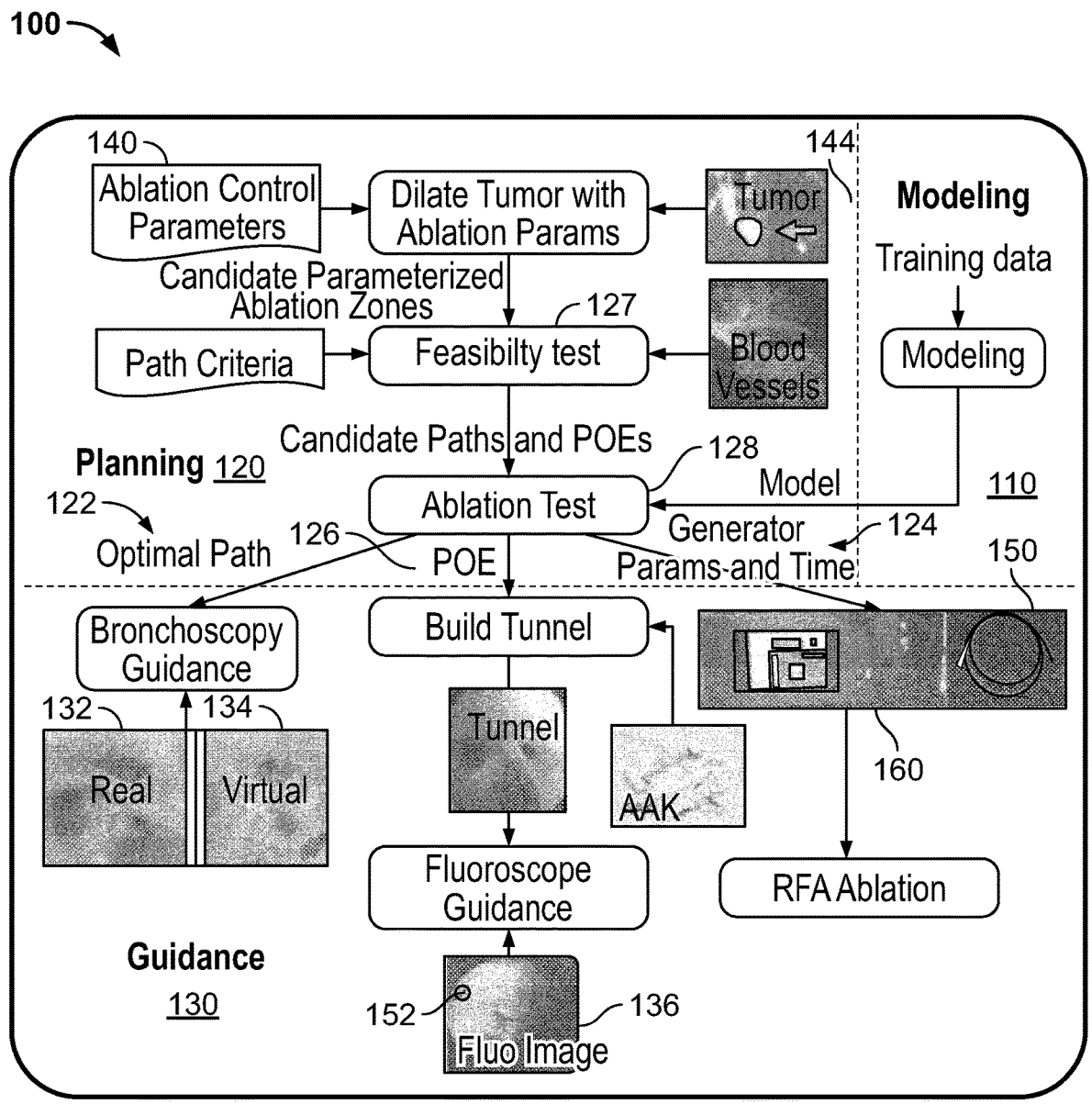
FIG. 1 is framework diagram of an ablation planning and guidance system in accordance with an embodiment of the invention.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. It is also to be appreciated that unless defined otherwise, all technical and scientific terms used herein have the same meaning as commonly understood by one of ordinary skill in the art to which this invention belongs.

Described herein are endoscopic-based planning and treatment systems for ablating centrally located targets including but not limited to targets that are otherwise inaccessible via a percutaneous approach. In an exemplary application, an ablation applicator is inserted through the bronchoscope/extended working channel to reach the target site. The ablation applicator may be used during interventional bronchoscopy procedures as determined by the physician performing the bronchoscopy.

System Framework

FIG. 1 illustrates an overview of a system framework 100 in accordance with an embodiment of the invention. The system 100 assists a physician to plan and carry out an ablation procedure based on predictive modeling. As shown in FIG. 1, the system 100 includes three subsystems: modeling 110, planning 120, and guidance 130.

The modeling subsystem 110 serves to learn the relation between candidate energy delivery parameters 140 of an applicator 150, described further herein, and ablation zone or target coverage dimensions based on experimental training data. The learned or trained model is used as an input to the planning subsystem 120, described herein.

The planning subsystem 120 serves to find the optimal airway path, point-of-entry (POE) of the tunnel leading to the target, and optimal applicator energy generator parameters 160 for the applicator to reach and ablate the lesion as desired by the physician.

The guidance subsystem 130 serves to assist the physician reach the target or navigate the physician to the target. In the guidance subsystem 130 shown in FIG. 1, bronchoscopic image 132, virtual bronchoscopic image 134, and fused-fluoroscopy guidance 136 are shown to assist the physician in delivering the applicator 150 to the target 152 via the planned route and applicator treatment parameters.

Figure 2:
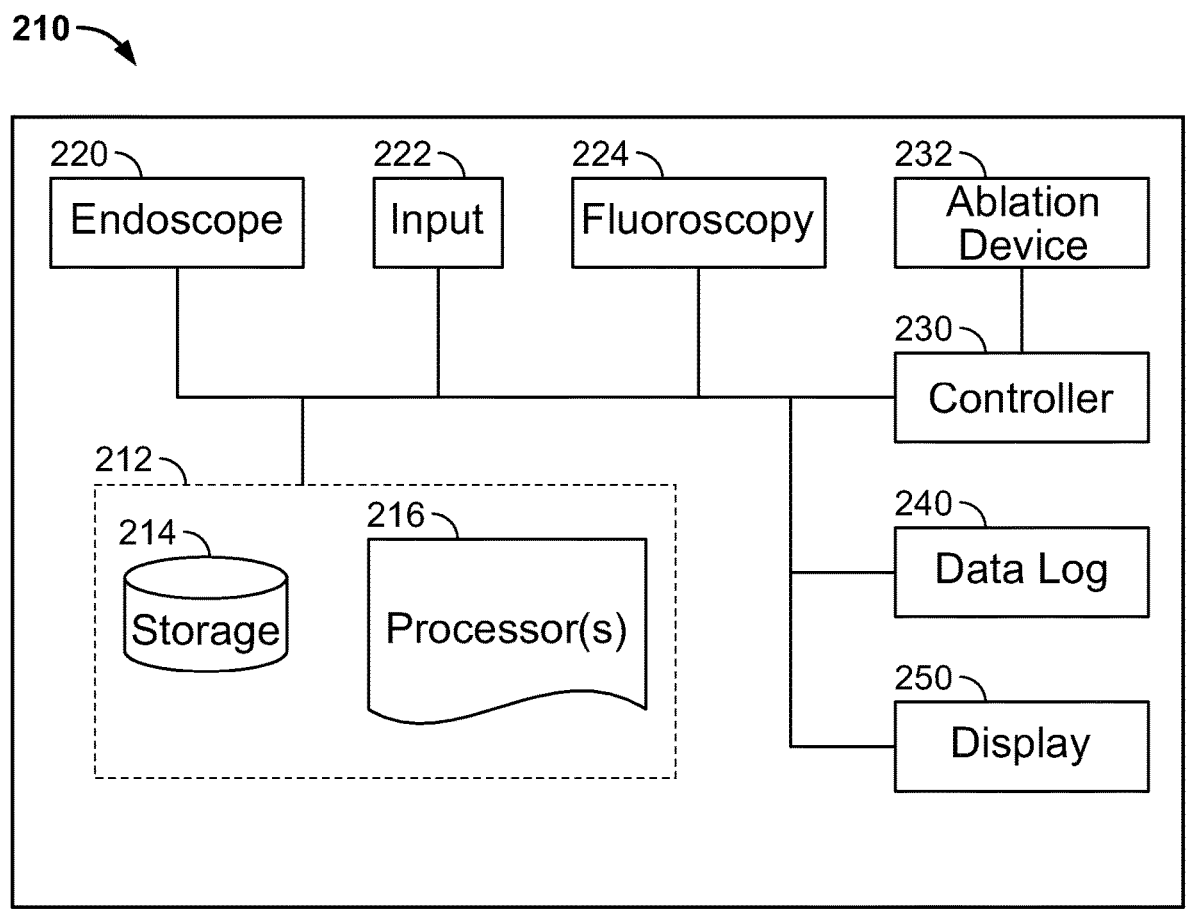
FIG. 2 is a block diagram of an ablation planning and guidance system in accordance with an embodiment of the invention.

FIG. 2 is block diagram of an exemplary system 210 for planning and ablating a target tissue in a body organ. A computer, server, or tablet 212 may include one or more processors 216 operable or programmed to carry out the actions described herein for each of the subsystems (or sometime referred to herein as engines or modules), and a storage 214 for holding information for carrying out the invention. Examples of information which may be stored or recorded on the storage 214 include but are not limited to anatomical constraints such as blood vessels, the pleural membrane, and organs or obstacles to avoid, bronchoscope parameters such as outer diameter, total length, and maximum bend radius, and physician inputs such as maximum distance from the airway to the target or other metrics.

The system 210 is shown including inputs 222. The inputs may be a wide range of inputs including but not limited to image data of the patient, physician inputs as described above, equipment or tool inputs and specifications of the devices for the anticipated ablation procedure. An example of a device for carrying out the input to the computer is a user interface such as a touch screen display or keyboard.

In embodiments, a complete set of 3D image data (e.g., pre-acquired CT data) of the patient is delivered to the computer and the computer is programmed to segment the lungs, blood vessels and regions of interest. Segmentation may be performed, for example, as described in U.S. Pat. No. 9,672,631 herein incorporated by reference in its entirety.

The system 210 is shown with an endoscope 220 such as a bronchoscope which is in communication with the computer 212. In embodiments, the processor is programmed to receive the real time bronchoscopic image data from the endoscope and register the real time bronchoscopic image data with a virtual bronchoscopic image generated from the CT image data. Bronchoscopy registration and guidance may be performed as described in, for example, U.S. Pat. Nos. 7,889,905 and 7,756,563, each of which is herein incorporated by reference in its entirety.

The system 210 is shown with fluoroscopy 224 such as a C-arm fluoroscopy unit which is in communication with the computer 212. In embodiments, the processor is programmed to receive the real time fluoroscopy image data from the fluoroscopy unit and register the real time fluoroscopy image data with a virtual fluoroscopy image generated from the CT image data. Fused or augmented images may be displayed based on the registration. Fluoroscopy registration and guidance may be performed, for example, as described in U.S. Pat. Nos. 9,265,468; 9,875,544; and 9,886,760, each of which is herein incorporated by reference in its entirety.

With reference again to FIG. 2, output from the processor may vary. In embodiments, output is sent to a display 250 for the physician to consider. In other embodiments, output may be in the form of instructions or signals which are delivered directly to a controller 230 which is used to activate and power the ablation device or ablation applicator 232. System 210 also shows output in the form of a data log 240.

Ablation Applicator

Figure 3A:
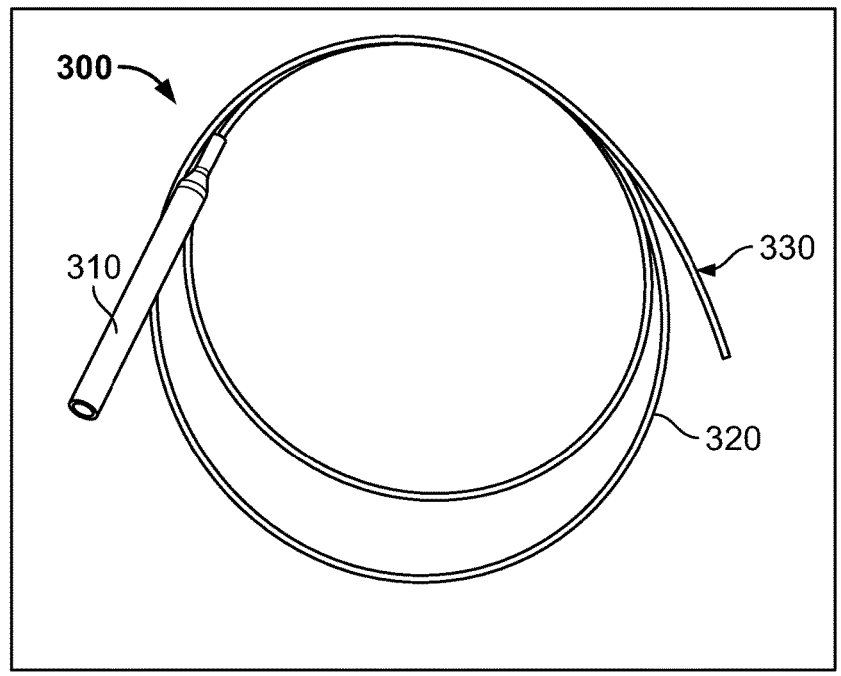
FIG. 3A is an illustration of a monopolar RFA catheter.

FIG. 3A shows an ablation device or applicator 300 in accordance with an embodiment of the invention. Applicator 300 is shown with a proximal handle 310, an elongate flexible shaft 320, and a distal end section 330. The flexible shaft 320 has dimensions and flexibility such that it may be advanced through the working channel of a bronchoscope to a target site within the upper airway or tracheobronchial tree. In embodiments, the shaft is comprised of a nitinol wire covered by insulation tubing to prevent kinking and facilitate pushability during tortuous bronchoscopic navigation.

Figure 3B:
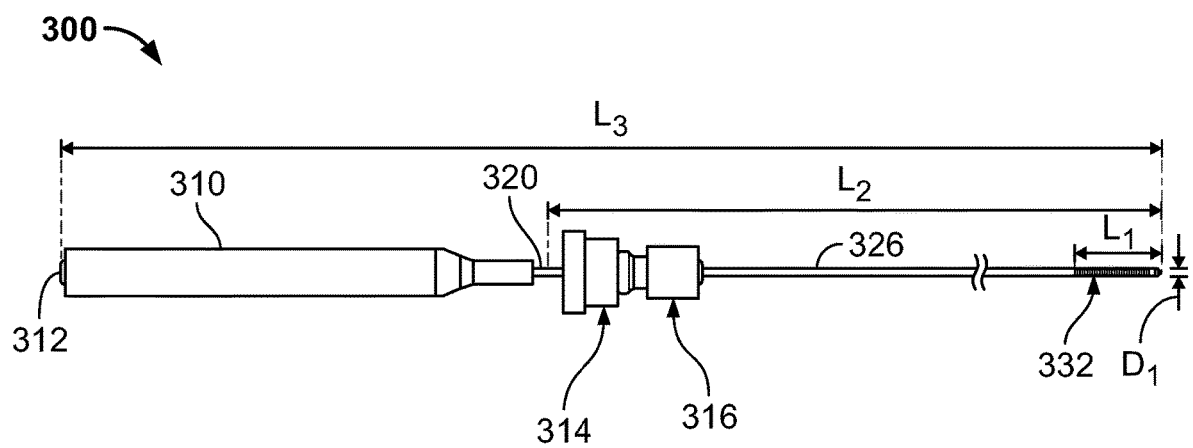
FIG. 3B is a partial enlarged view of a delivery sheath and the RFA catheter shown in FIG. 3A inserted therein.

With reference to FIG. 3B, the applicator 300 is shown advanced into a delivery sheath 326 until the distal section 330 of the applicator is protruding from the end of the sheath. Particularly, electrode 332 is shown protruding from the end of the sheath. When an electrical connector 312 (e.g., a standard male banana plug) at the proximal end of handle is connected to the controller (not shown, and also referred to herein sometimes as a generator), and applicable grounding pads or return electrode are applied to the patient body as is customary for monopolar-based RF ablation, a controlled radiofrequency (RF) energy can be delivered to the target site. An example of an electrosurgical generator is ERBE VIO 300 D, manufactured by Erbe USA, Marietta, Georgia, USA.

The dimensions of the applicator and electrode may vary. In embodiments, the applicator electrode 332 has a diameter $D_1$ less than 2 mm, in some embodiments, between 1.6-1.9 mm, and in one embodiment about 1.8 mm. In embodiments, the applicator electrode 332 has a length $L_1$ less than 20 mm, in some embodiments, between 16-20 mm, and in one embodiment about 18 mm.

In embodiments, the shaft length $L_2$ ranges between 1400-1500 mm, and in one embodiment between 1400 and 1500 mm. In embodiments, the applicator total length $L_3$ is preferably greater than 1500 mm, and in embodiments ranges from 1500-1550 mm, and in one embodiment about 1540 mm.

Method for Planning Ablation

Figure 4:
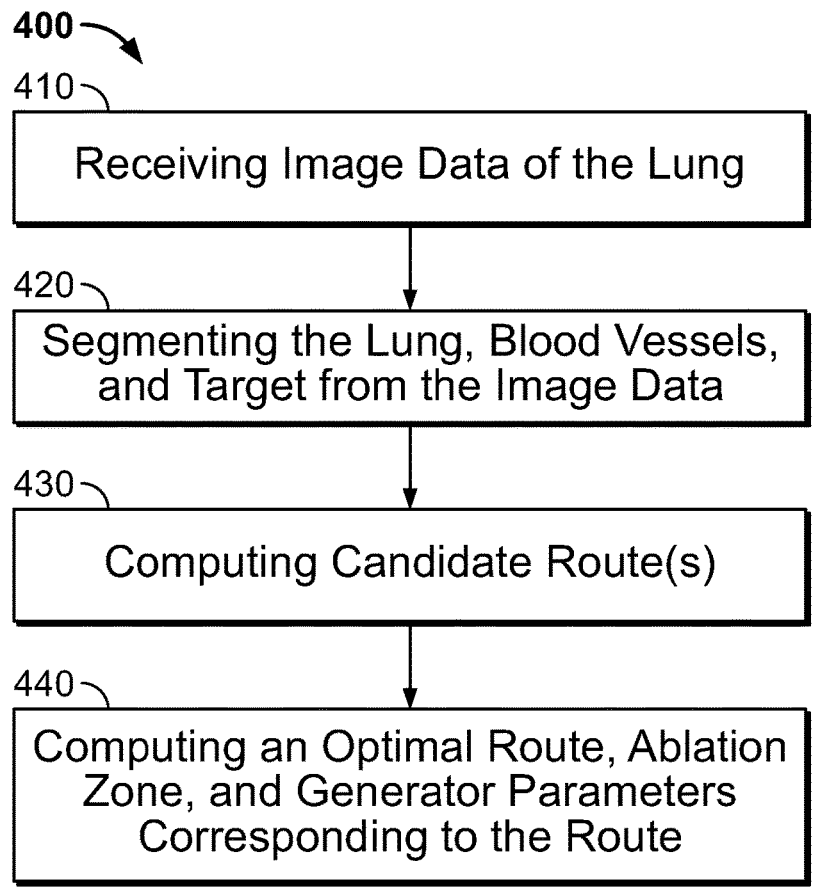
FIG. 4 is a flow chart illustrating a method for planning ablation in accordance with an embodiment of the invention.

FIG. 4 is an overview of a method 400 for planning a tumor ablation in accordance with an embodiment of the invention.

Step 410 states to receive image data of the lung. Image data as described herein may include pre-acquired CT image data of the patient.

Step 420 states to segment the lung and other critical structures such as the blood vessels and target. Segmentation may be performed as described in, for example, U.S. Pat. No. 9,672,631 herein incorporated by reference in its entirety.

Step 430 states to compute the candidate route(s) to the target. As described herein, this computation is based on various information including anatomical constraints, device parameters or specifications, and physician preferences. In a sense, a feasibility test is performed to determine whether bronchoscope and applicator can safely access or reach the target. Examples of route planning techniques are also described in U.S. Pat. Nos. 8,709,034 and 9,037,215, each of which is incorporated by reference in its entirety.

Step 440 states to compute the optimal route and its related ablation zone or region and the generator parameters. The ablation zone is computed as described herein and particularly, in embodiments, based on the anatomy, applicator characteristics, route, and various metrics as inputs in a predictive model. The output is the ablation zone and ablation treatment parameters including, for example, power, ablation time.

Examples of computed routes to the target and target ablation zones are shown in FIG. 12 where RFA1, RFA2, RFA3 and RFA4 correspond respectively to four different metrics: best score, best tumor coverage, minimal distance between the airway wall and the target, and minimal ablation treatment time. By "best score", it is meant the weighted sum of the tumor coverage, the minimal distance and the treatment time.

Figure 13:
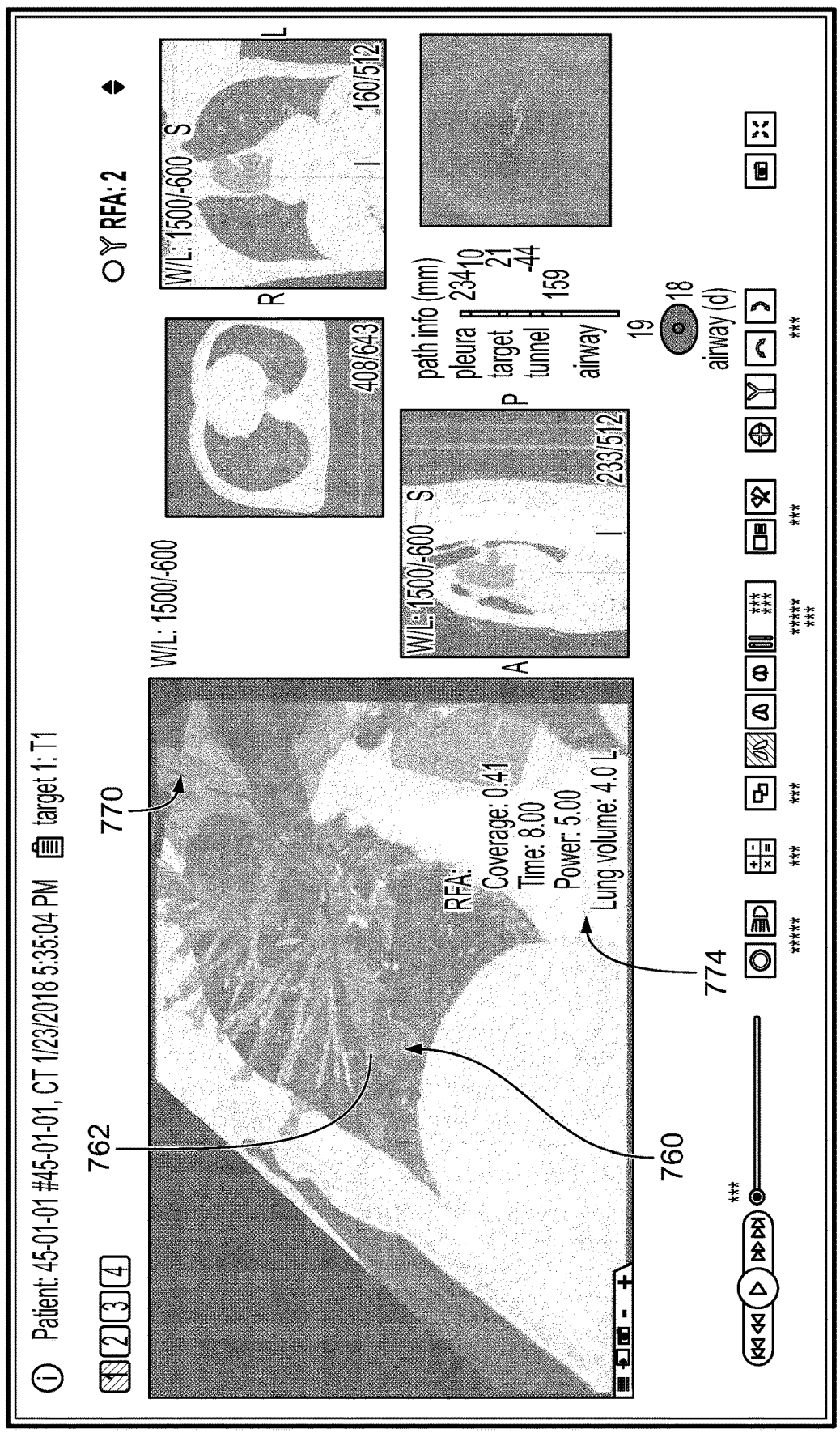
FIG. 13 is an illustration of a first planning route shown in FIG. 12, and an enlarged view of tumor ablation coverage.

An enlarged view of a computed ablation zone is shown in FIG. 13. Particularly, FIG. 13 visually shows the estimated optimal path 770, POE and the ablation region 760 for a sphere-shaped tumor 762. Ablation parameters 774 are also listed including power limit, time.

Building/Training Modeling Subsystem

As stated above, a learned model is input to the planning engine and used to compute the ablation zone. In embodiments, the learned model was trained using ablation zone dimensions from ex vivo experiments as training data to build a machine-learning based model that provides the physician choices for radiofrequency energy delivery parameters to achieve desired tumor ablation such as a conformal tumor ablation.

In embodiments, during the model training phase, a non-linear regression is employed to create model mapping energy delivery parameters (e.g., applied power, Effect, and ablation time) to the ablation zone dimension. Compared to simulation-based approaches, and without intending to being bound to theory, the experimental approach is independent of tissue biophysical properties, which are unknown on a patient-specific basis. Additionally, to avoid overfitting, a cross validation can be employed to train the model using k-1 folds as training data and validate the model on the remaining part of the data. Once training is completed and the model is established, the ablation zone dimensions can be estimated using the given energy delivery parameters. The learned model in the modeling subsystem is an input of the planning subsystem, which performs the optimization to find the optimal energy delivery parameters for the identified target ablation zone.

Data Collection for Training

Figure 5A:
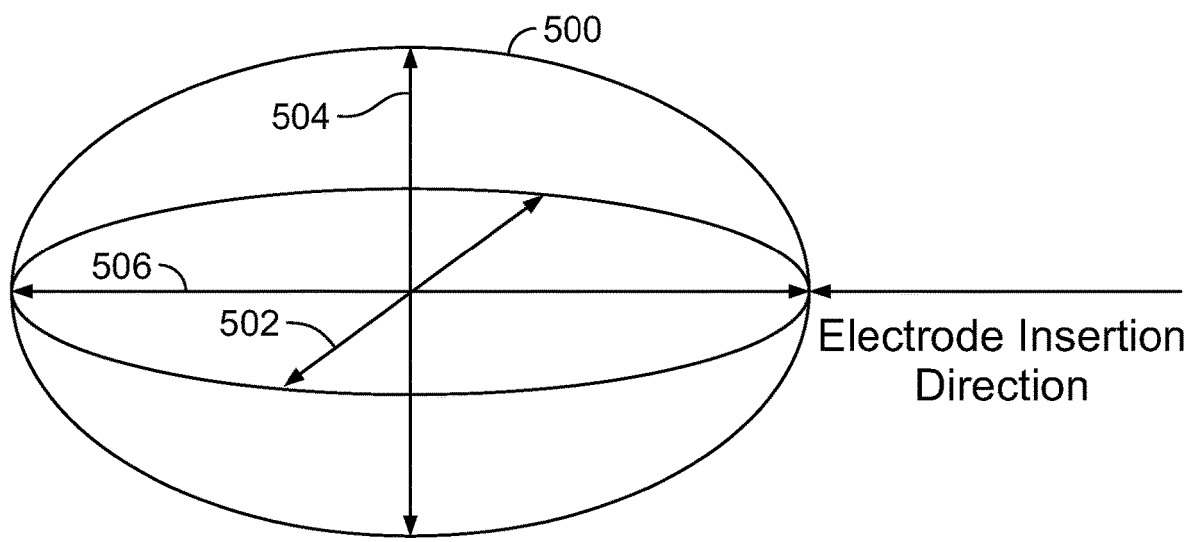
FIG. 5A is an illustration of a model of an ablation zone.

We conducted ablation experiments, described herein, on ex vivo beef liver to record multiple measurement pairs: (input, output). The input includes applied power, Effect (by "Effect" it is meant an integer to represent the ablation consequence such as Effect 1 means minimal coag and Effect 4 means maximal coag.) and ablation time. We defined the output as axis lengths of an ellipsoid 500 as shown in FIG. 5A. We assume the Minor axis 502 has the same length as the Minor axis 504. We recorded the length of the Major axis 506 and Minor axis 504. Two investigators carried out the experiments to account for measurement variation.

The steps of the procedure to collect the data are described below.

Remove fresh liver samples from cooler, place in fluid sealed bags, seal, and place sealed Ziploc bag in temperature controlled bath ~37 C.

Remove tissue sample from water bath, take out of fluid sealed bag, and measure temperature with a thermocouple. If temperature ~35-37 C, proceed with experiment below. Otherwise, place back in bag and continue warming.

Place tissue sample in test fixture.

Insert plastic catheters for guiding temperature probe placement.

Remove guiding needle and insert temperature sensors.

Record initial tissue temperature.

Remove temperature sensors.

Insert electrode of the applicator so tip is 6 cm below liver proximal surface.

Connect cable from generator to applicator handle.

Turn on generator and then wait 30 s.

Start treatment for a fixed time.

Turn off generator.

Slice tissue along the electrode.

Remove the electrode.

Take photos. One with ruler parallel to applicator, one with ruler perpendicular. Be sure that the ruler is well away from the ablation zone boundary.

Figure 7A:
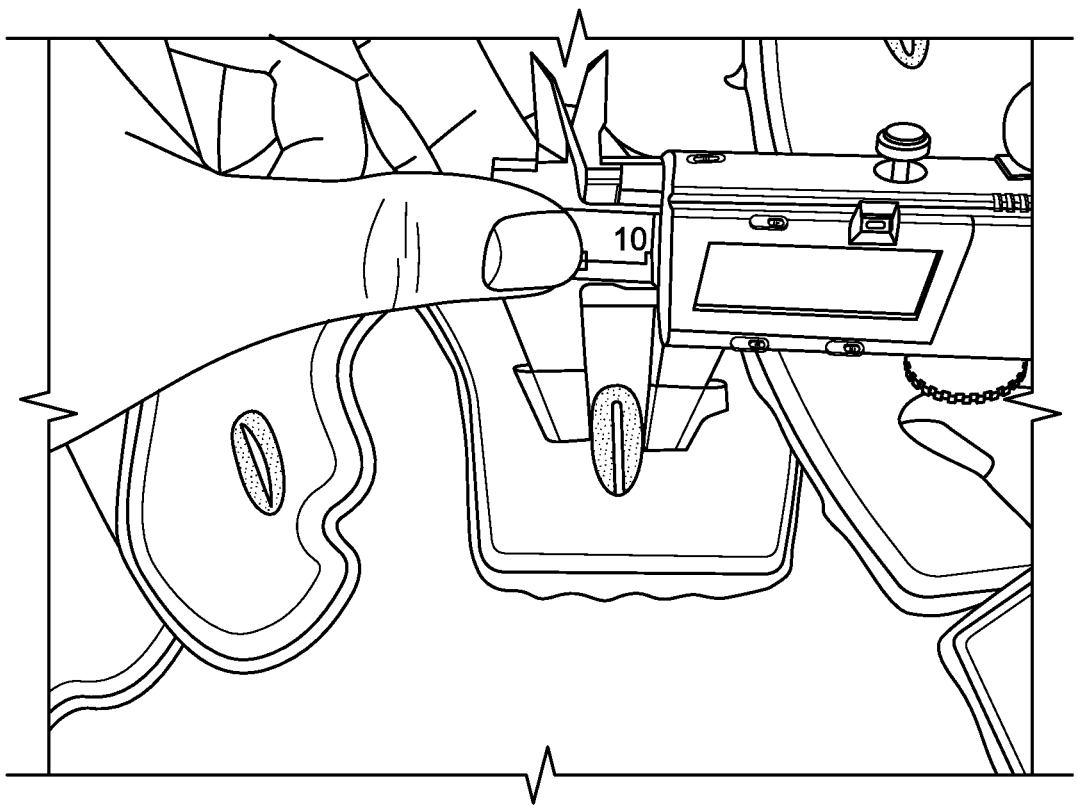
FIG. 7A is an illustration of measuring a minor axis length of a tissue specimen.

Measure ablation zone dimensions and note a) Short-axis diameter; and (b) the Long-axis diameter. An illustration of measuring the short or minor axis diameter is shown in FIG. 7A Non-Linear Regression Model As described above, in embodiments, a non-linear regression (supervised learning) is employed for modeling. The model employed is a combination of the regression coefficients and the predictor variables (e.g., applied power, the Effect and the treatment time). For the predictor variables, the applied power and the Effect are discrete variables, but the treatment time is a continuous variable. Thus, we conducted regression on the treatment time for each combination of the applied power and the Effect. For the response, we measured lesion major and minor axis length.

In this example, we conducted regression for each response and transformed the predictor variables with a polynomial. Higher order polynomials provide more flexible models. But higher order polynomials tend to be subjected to overfitting. To determine or choose an appropriate polynomial order, we iterate a number of possible (or candidate) orders 0, 1, 2, 3, and 4.

For each order: (a) Partition the original data into k equal sized subgroups, in which k−1 subgroups are used as training data and the remaining subgroup is used as testing data (b) Perform Ridge regression on k−1 subgroups to find regression coefficients. Here we use Ridge regression in order to make the coefficient estimator robust against outliers. (c) Perform testing on remaining subgroup to find the error between the predicted zone and the measurement zone. (d) Repeat k times with each of the k subgroups used once as the testing data and do average for the error. Then, we select the model with the smallest error as the final model. In embodiments, a method includes selecting from the plurality of possible (or candidate) models a final ablation model having the smallest error.

The k-fold cross-validation is a valuable way to examine the prediction accuracy of the model. It is suitable for the situation when there is insufficient data for training. As stated above, we partition the original data into k equal sized subgroup and then repeatedly use k−1 subgroups to do training and use the remaining subgroup (unseen data in the training) to do validation. The Mean squared error between the predicted zone and the measurement zone for all samples in the testing subgroup denotes how well the model predicts this subgroup. We do average for k times to produce one measurement to denote the performance of the model prediction.

After we finish the modeling, we can predict the ablation zone given energy delivery parameters. However, in clinical practice, we want to know what the best energy delivery parameters given a target ablation zone. Not all modeling has an analytical solution, so we use numerical method to find the energy parameters which have the closest predicted ablation zone with the target zone. Based on our ex vivo experiments, described herein, the ablation zone progression exhibits a pattern that the ablation zone increases fast at the beginning and then gradually slowly and then begins to decrease. Without intending to being bound by theory, given a target zone, there might be multiple time points corresponding with this target zone. Thus, we used a numerical method to find the time point, and we limited the search to the first-time point.

Although embodiments of the invention employ a non-linear regression curve fit or model, the invention may employ other types of models or algorithms to predict the ablation zone. Examples of algorithms include machine learning and artificial intelligence-based algorithms including but not limited to neural networks and convolutional neural networks, Regression tree, and Support Vector Machines.

For example, in embodiments, the ablation zone model is a deep learning model and developed as follows: 1.) Separate data into training dataset, validation dataset, and test dataset; 2.) The input layer includes the treatment time, biophysical parameters and energy deliver parameters and the output layer is the annotated ablation zone on CT. Use one hidden layer; 3.) Use ReLU as the activation function; 4.) Use Mean Square Error as the loss function; and 5.) Use backpropagation to calculate the gradient. Based on the above mentioned settings, we train the neural networks ("nets") on the training dataset and validate the nets on the validation dataset to estimate the nets weights and bias and hyper parameters such as, e.g., the regularization parameter. Finally, we test the nets on the test dataset. Although only a few techniques are described to develop an ablation model using deep learning, other techniques may be employed and the invention is only intended to be limited as set forth in the recited claims.

Ablation Planning Subsystem

As discussed herein, and with reference again to FIG. 1, output of the ablation planning engine or subsystem is an optimal path 122 to the target and energy delivery parameters 124. In embodiments, the planning subsystem computes: (1) the optimal airway path 122 to bronchoscopically deliver the applicator to the POE of the tunnel, (2) the POE 126 of the tunnel to deliver the applicator through the tunnel to the target, and (3) the energy delivery parameters 124 suited for conformal ablation of the target.

Inputs to the planning engine include image data such as pre-procedural high resolution CT scans. After segmenting the tumor and neighboring critical structures, an ablation target 144 will be prescribed (e.g., the tumor boundary plus a clinician-specified circumferential margin of normal tissue). Based on the ablation target, a feasibility test 127 will be conducted to verify if there is a path which can (1) allow the bronchoscope to reach POE based on predefined path criteria such as the airway diameter, bronchoscope tip diameter, and bronchoscope bending angle and (2) access the target from an airway, without crossing vessels or other critical structures.

After the feasibility test 127, an ablation test 128 is performed. The ablation test 128 receives as inputs candidate paths, POEs and modeling, and for each candidate path and POE, estimates treatment parameters 124 including the energy deliver parameters, the treatment time, the ablation area and the distance from the POE to the surface of the target. In embodiments, the path, POE and energy deliver parameters corresponding to the minimal time, maximal ablation coverage, the shortest distance from the airway to the target and their combination (the best score) will be advised to surgeons.

Figure 5B:
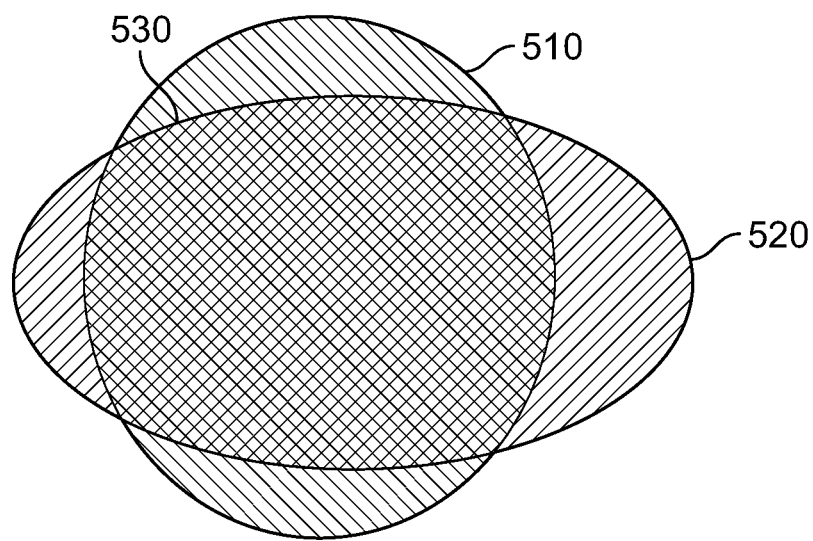
FIG. 5B is an illustration of tumor ablation coverage.

In embodiments, an output of the planning engine is the energy delivery parameter corresponding to the maximum ablation coverage. In embodiments, and with reference to FIG. 5B, ablation coverage (COV) is defined as the product of two ratios, or COV=ATT*ATAR, where the first ratio (ATT) is the ablated tumor size 530 to the tumor size 510; and a second ratio (ATAR) is the ablated tumor size 530 to the ablated region size 520 In embodiments, this metric COV is used to choose the treatment path which ablates as much of the tumor as possible while leaving remaining as much of the normal tissue as possible. In embodiments, the metric COV ranges from 0 to 1.

In embodiments, as discussed herein, the planning subsystem 120 is based on a learned model, trained with ex vivo experimental data. Without intending to being bound to theory, due to the difference in biophysical conditions between ex vivo animal beef (without tumor) and in vivo human lung with a tumor, it is anticipated that there will be variations in observed ablation zone dimensions. Rather than providing a precise estimate of the expected in vivo ablation zone dimensions, the planning subsystem and module described herein provides physicians a tool for comparative assessment of energy delivery parameters and anticipated ablation zone extents.

In embodiments, the physician can adjust energy delivery parameters, and specifies the parameters clinically applied by the generator. Similarly, in embodiments, the planning module requires the physician to approve or adjust the route for accessing the tumor suggested by the planning module.

Guidance Subsystem

The guidance subsystem 130 or engine described herein serves to assist the physician to safely create a tunnel from the bronchial airway, through parenchymal tissue to the target, and without traversing vasculature or puncturing the pleural membrane.

Figure 6A:
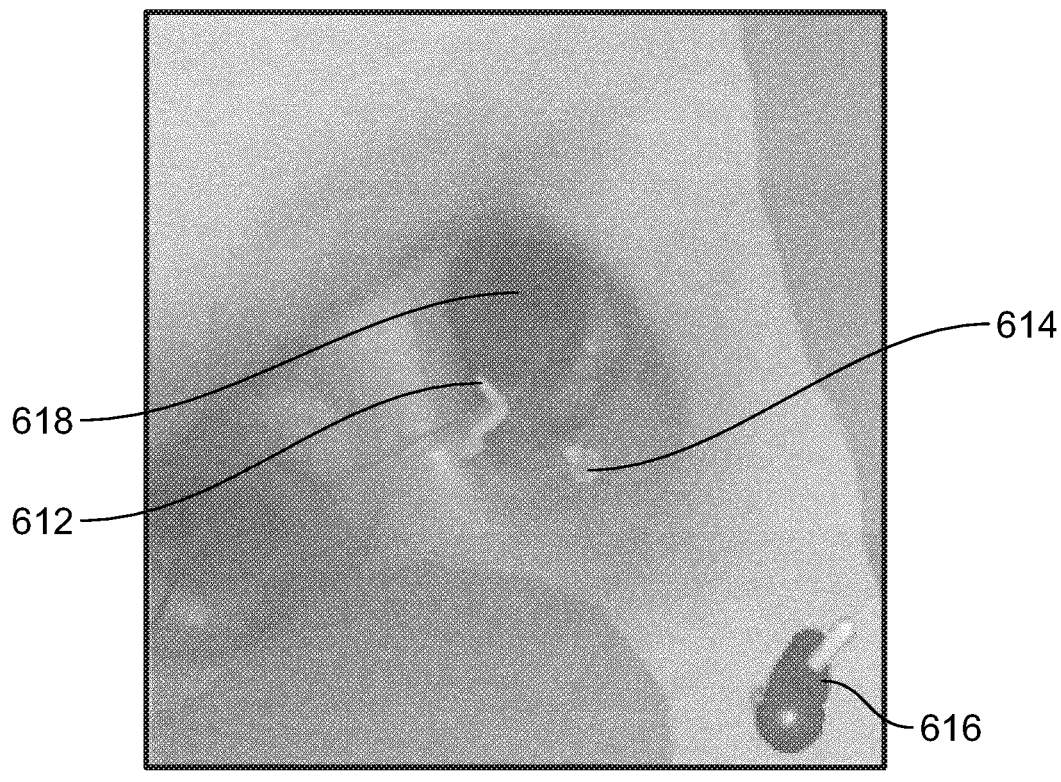
FIGS. 6A-6F are illustrations of steps of a method for guiding a catheter to the target.

With reference to FIG. 6A, an acquired bronchoscopic image is augmented 610 with an optimal airway path 612 to guide the applicator to the POE 614. Optionally, a compass 616 and airway centerline 618 are shown to provide additional information to assist the physician during the procedure. The icons or symbols shown in the augmented bronchoscopy view may vary. In the embodiments shown in FIG. 6A, the POE is indicated using a 3D arrow which provides both location and direction information.

Figure 6B:
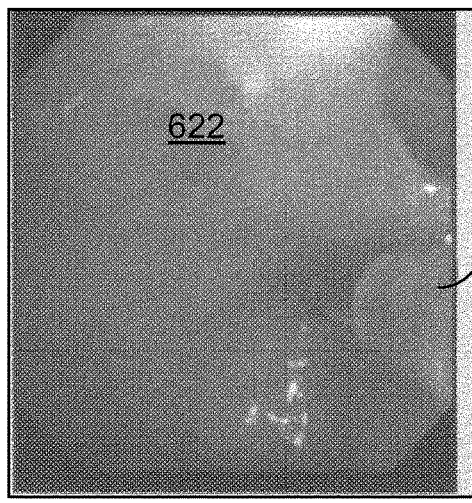

Next, with reference to FIG. 6B, a hole is created at the POE through the airway wall 622 with a piercing member 624. An example of a piercing member is needle or wire.

Figure 6C:
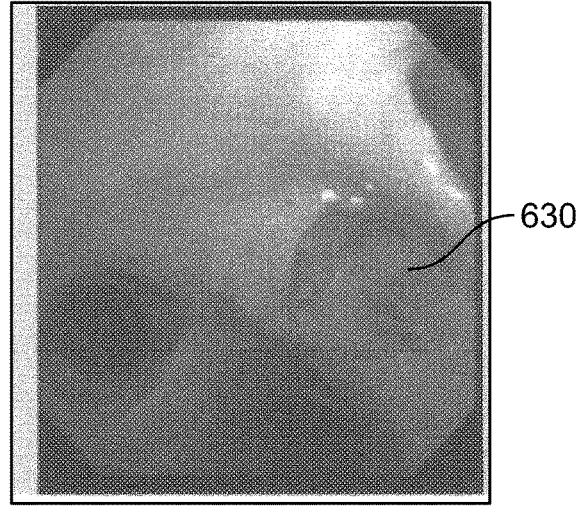

FIG. 6C shows dilating the hole with a dilating member. Particularly, an inflatable balloon 630 is shown in an expanded state in the hole.

Figure 6D:
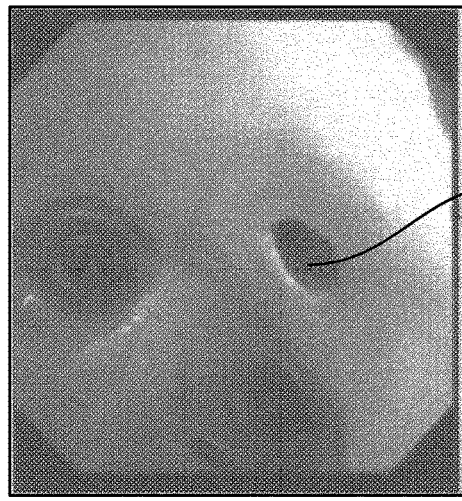

FIG. 6D shows the instruments removed, leaving an enlarged hole 634

Figure 6E:
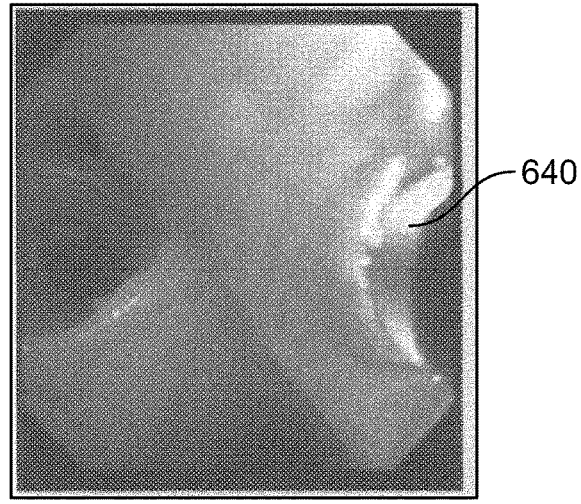

FIG. 6E shows a dissecting catheter 640 advanced through the enlarged hole. The dissecting catheter may comprise a stylet or obturator coaxially surrounded by an outer guiding sheath. In embodiments the physician advances the dissecting catheter 640 to the target under fluoroscopic guidance. Once positioned, the stylet is withdrawn from the guiding catheter to create an open tunnel from the airway to the target in accordance with the route(s) suggested in the planning engine. A tunnel is thus created with guiding sheath to deliver the ablation applicator from the airway through parenchymal tissue to the target site.

In alternate embodiments, the inner stylet or wire is initially navigated from the airway to the target, and the guide sheath is advanced over the wire along the stylet. Once the sheath is positioned as desired, the stylet is removed leaving an open tunnel for performing the procedure.

A fine technique to create a tunnel through the lung tissue to the target is described in U.S. Pat. Nos. 8,709,034 and 8,784,400. An example of a set of instruments for creating a tunnel through the lung to the target is also commercially available and sold under the brand Archimedes Access Kit, manufactured by Broncus Medical Inc. (San Jose, California). An example of a commercially available system for planning, navigating, and tunneling to the target is the Archimedes System, also manufactured by Broncus Medical Inc.

Figure 6F:
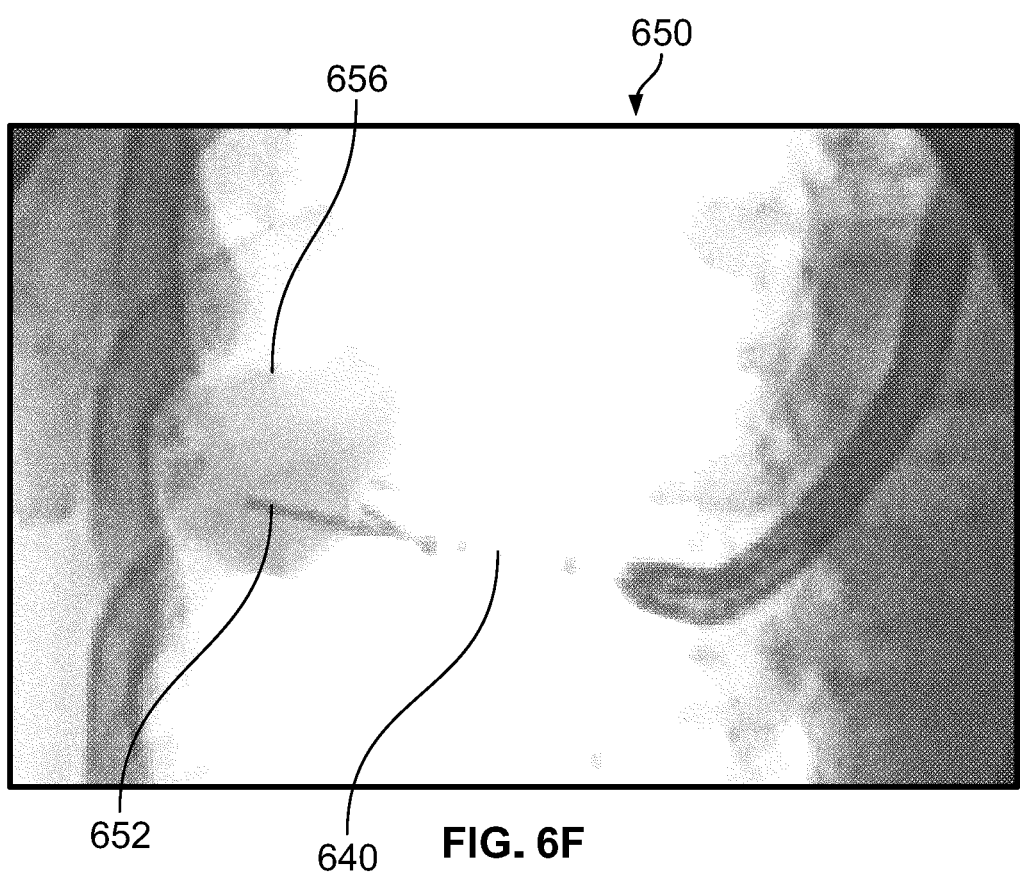

FIG. 6F depicts a co-registered (virtual image with CT image) fluoroscopic image 650 showing the electrode 652 of the ablation applicator being guided through the sheath 640 to the target 656. Once the electrode 652 is appropriately positioned, energy is applied and the ablation commences in accordance with the suggested ablation parameters from the planning module or as modified by the physician.

EXAMPLE

We performed ablation testing on ex vivo beef specimens for various ablation times given a power limit and Effect combination. An RFA applicator and generator as described above in connection with FIG. 3 was used to create each of the lesions Table 1, below, shows the testing matrix for the example. The Power limit was 5 W and the Effect was 1.

TABLE 1

| Controlled Variable | Specimen Size | 91.2 mm × 71.6 mm × 26.3 mm |
|---|---|---|
| | Power Limit | 5 W |
| | Effect | 1 |
| Independent Variable | Ablation Time | From 2 to 8 minutes |
| | | Interval of 30 seconds |
| Dependent Variable | Ablation Zone | 2 observers will measure: |
| | | Major axis |
| | | Minor axis |

The minor and major axis were measured following ablation. FIG. 7A illustrates our technique for measuring a Minor axis length of one lesion using electronic calipers. Each measurement was performed by two investigators.

Figure 7B:
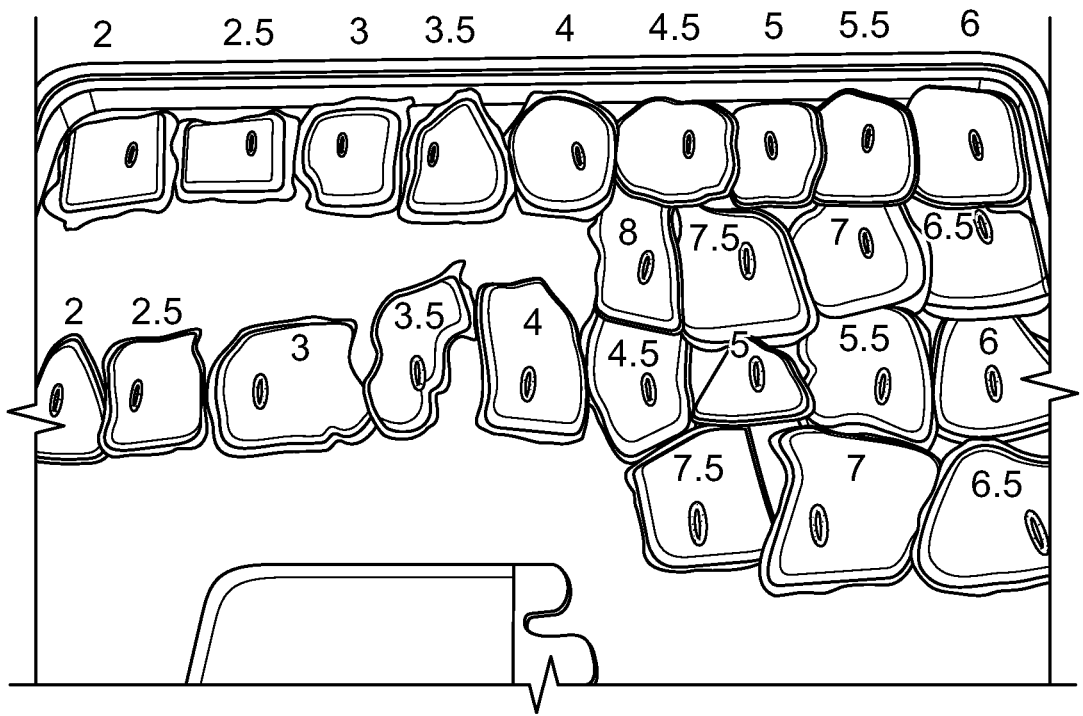
FIG. 7B is an illustration of ex vivo beef RFA ablation samples.

FIG. 7B shows the ex vivo beef RFA samples after testing, and their corresponding treatment times. Results of the experiment including the treatment time, lesion major and minor axis length are listed in Table 2.

TABLE 2

| Treatment Time (min) | Major Axis (YL) | Major Axis (JI) | Mean Major Axis | Minor Axis (YL) | Minor Axis (JI) | Mean Major Axis | Average// Max Power |
|---|---|---|---|---|---|---|---|
| 2 | 18.7 | 18.8 | 18.75 | 3.8 | 4.8 | 4.3 | n/a |
| 2.5 | 19 | 19.8 | 19.4 | 4.1 | 5 | 4.55 | 3//5 |
| 3 | 20 | 2.2 | 21 | 5.5 | 6 | 5.75 | n/a |
| 3.5 | 20 | 21.5 | 20.75 | 8.5 | 7 | 7.75 | 3//5 |
| 4 | 21.8 | 22.3 | 22.05 | 10.1 | 9.8 | 9.95 | 3//5 |
| 4.5 | 21.6 | 22.3 | 21.95 | 9.6 | 9.2 | 9.4 | n/a |
| 5 | 18.7 | 22 | 20.35 | 9.6 | 9.2 | 9.4 | 3//5 |
| 5.5 | 24.4 | 23.4 | 23.9 | 9.6 | 9.2 | 9.4 | n/a |
| 6 | 23 | 23 | 23 | 10 | 9.8 | 9.9 | 3//5 |
| 6.5 | 23 | 23 | 23 | 13.8 | 12.5 | 13.15 | 3//5 |
| 7 | 24.3 | 23 | 23.65 | 13.3 | 12 | 12.65 | 3//5 |
| 7.5 | 22.5 | 21.3 | 21.9 | 11.2 | 10.8 | 11 | n/a |

Figure 8:
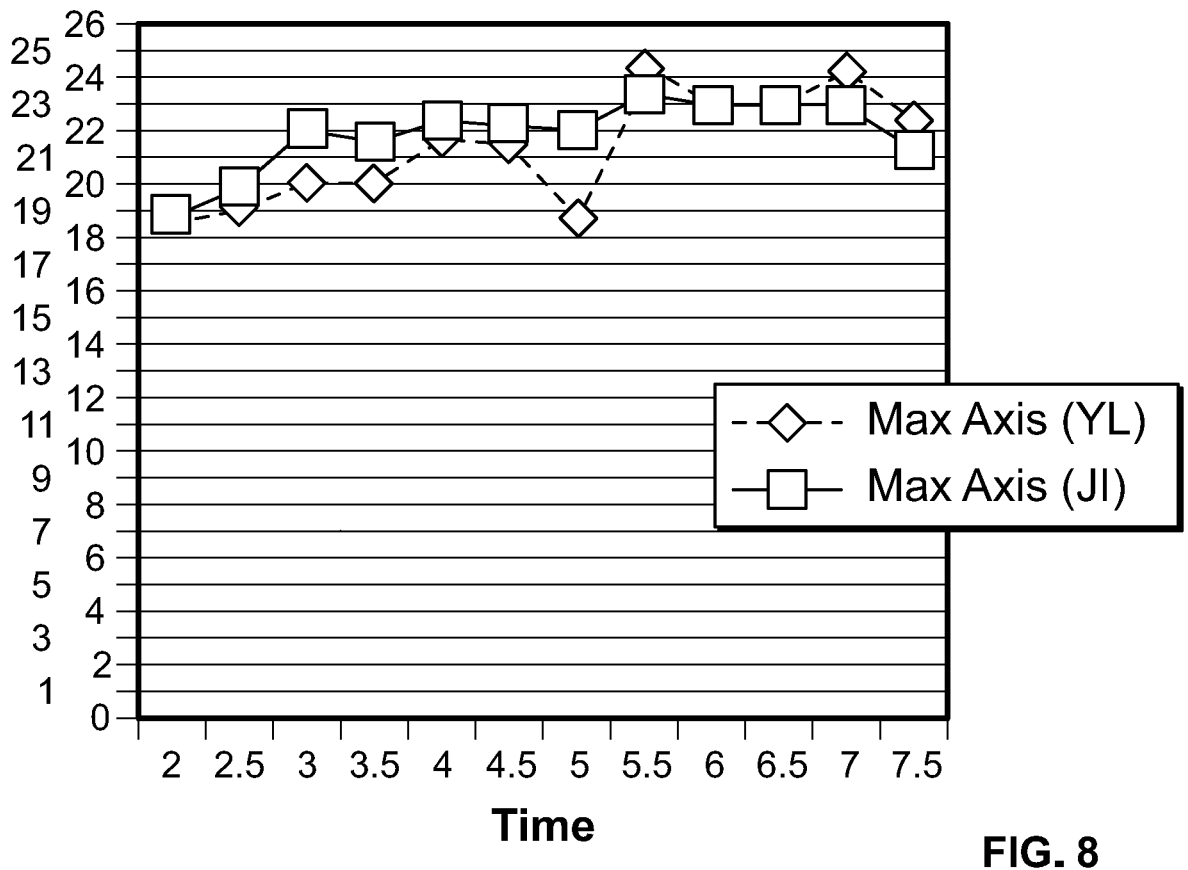
FIG. 8 is a plot of time vs lesion major axis.

FIG. 8 is a first plot of treatment time vs lesion major axis length. The plot evidences a non-linear pattern. Particularly, we observe: (a) the major axis slowly increased in the time beginning and then decreased at 5 minutes ablation. However, there was a significant measurement difference at 5 minutes between both investigators; (b) a large increment in the major axis is observed in ablation time from 5 to 5.5 minutes (major axis increased about 3 mm in 30 seconds);

and the longest major axis was reached at 5.5 minutes ablation, and then the lesion axis length decreased.

Figure 9:
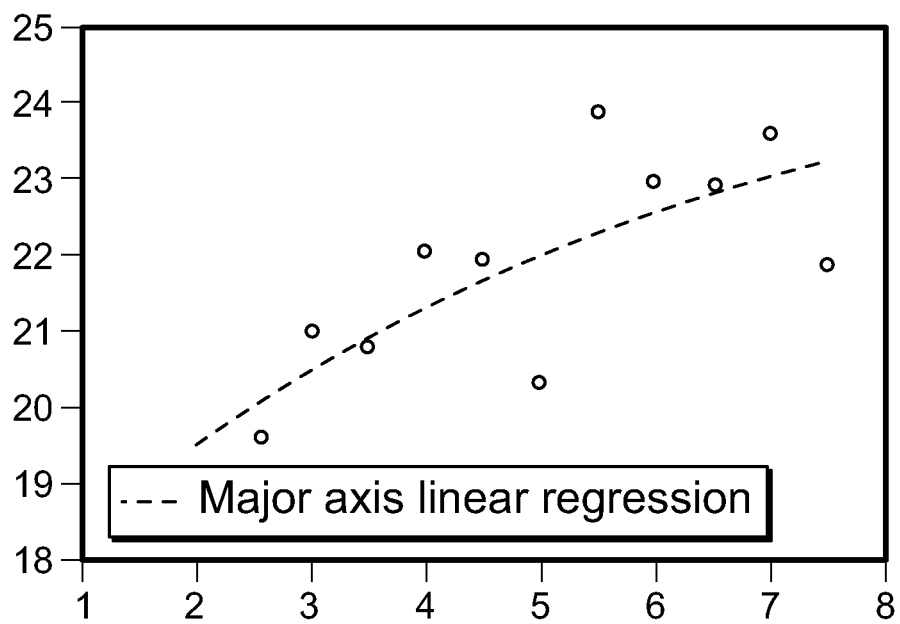
FIG. 9 is a regression curve fit for the data shown in FIG. 8.

We performed a non-linear regression with L2 regularization (ridge regression) on the data shown in FIG. 8. The regression curve for the major axis vs. time is shown in FIG. 9. The mean square error is 0.80 and the variance is 0.68. Here, the degree of the polynomial features is 3, which was determined by cross-validation.

Figure 10:
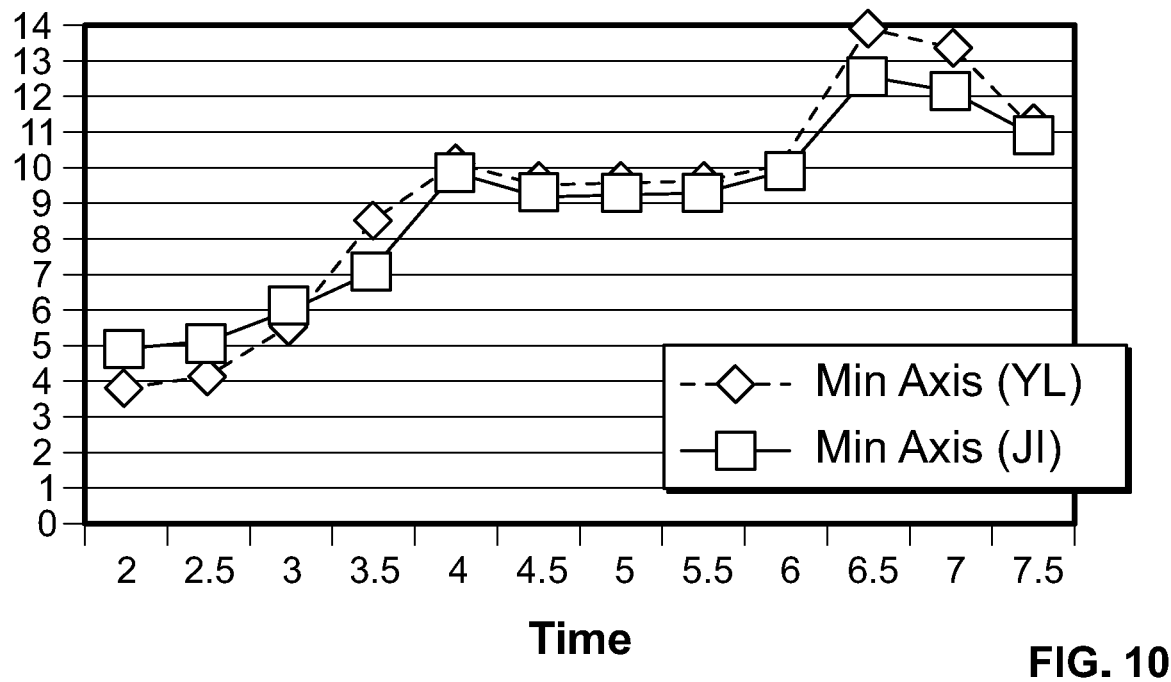
FIG. 10 is a plot of time vs. lesion minor axis.

FIG. 10 is a second plot of treatment time vs lesion minor axis length. The plot evidences a non-linear pattern. Particularly, we observe: (a) the Minor axis generally increased with increasing ablation time but slight decreased is seen from minute-4 to minute-4.5 ablation time and minute-6.5 to minute-7; (b) a large increment of minor axis is observed from minute-3 to minute-4 ablation time and minute-6 to minute-6.5, and (c) the longest minor axis was at 6.5 minutes ablation, and then axis length decreased.

Figure 11:
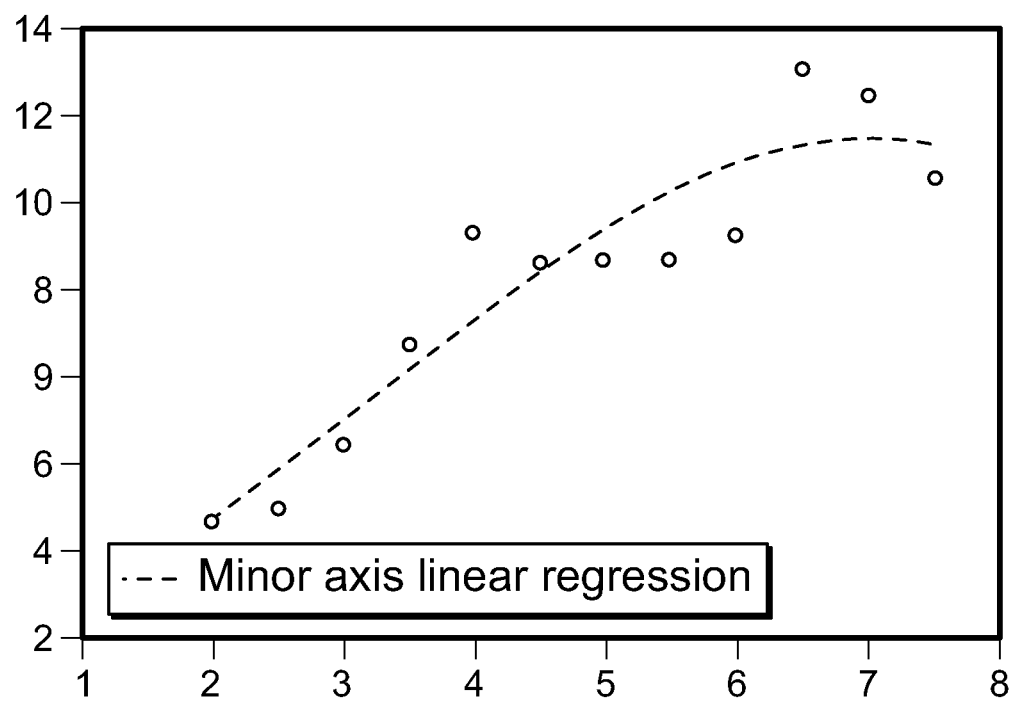
FIG. 11 is a regression curve fit for the data shown in FIG. 10.

We performed a ridge regression on the data shown in FIG. 10. The regression curve is shown in FIG. 11. The mean square error is 0.96 and the variance is 0.87.

Compared to the major axis regression curve, both of the mean square error and variance of the minor axis regression curve are relatively large. Without intending to being bound by theory, the reason the minor axis regression curve has larger variance is because the Minor axis length is smaller than the major axis length, and the minor axis length has a relatively large fluctuation as a function of time, which can also be visually observed in the tissue specimens shown in FIG. 7B.

Alternative Embodiments

Other modifications and variations can be made to the disclosed embodiments without departing from the subject invention.

For example, embodiments of the invention include ablation devices and energy-delivering modalities other than that described above. Energy delivery modalities include without limitation use of condensable vapor, microwave energy, and cryo energy.

Additionally, although the above described RF applicator has been generally described having a mono-polar configuration, the invention is not so limited and can include alternative electrode configurations such as but not limited to bi-polar type electrode configurations.

Other modifications and variations can be made to the disclosed embodiments without departing from the subject invention.

The invention claimed is:

1. A bronchoscopic-based system for planning to ablate a target tissue in a lung of a patient with an ablation applicator comprising:
   a storage for receiving image data of the lung of the patient including the target tissue to be ablated; and
   a processor programmed and operable to:
      compute, based on the image data of the lung, at least one candidate path for the ablation applicator to be advanced through the airway of the patient to a candidate point of entry (POE), and from the POE to the target tissue;
      select a learned ablation model from a plurality of candidate models based on a set of candidate ablation parameters and at least one characteristic of the target tissue, wherein the plurality of candidate models are based on past experimental data, and wherein the past experimental data includes measurements from ablation testing on sample tissue; and
      compute an ablation zone based on said learned ablation model to maximize ablation coverage of the target tissue for each said candidate path.

2. The system of claim 1, wherein the set of candidate ablation parameters are selected from the group consisting of power, frequency, and treatment time.

3. The system of claim 2, further comprising computing the plurality of candidate ablation treatment parameters for each said candidate path to the target tissue.

4. The system of claim 1, further comprising a bronchoscope, the bronchoscope comprising a working lumen through which the ablation applicator may be advanced.

5. The system of claim 1, further comprising the ablation applicator.

6. The system of claim 5, wherein the ablation applicator is adapted to raise a temperature of the target tissue to a lethal temperature.

7. The system of claim 6, wherein the ablation applicator is a radio-frequency energy catheter.

8. The system of claim 1, wherein the target tissue is a tumor, and the processor is operable to compute the set of candidate ablation parameters which maximize ablation coverage of the tumor.

9. The system of claim 1, wherein the processor is operable to compute a maximum tumor ablation coverage by maximizing a ratio (COV) defined as a product of ATT and ATAR where ATT is ablated tumor size to tumor size and an ATAR is the ablated tumor size to ablated region size.

10. The system of claim 1, wherein the plurality of candidate models is based on a plurality of different types of tissue.

11. The system of claim 1, wherein the learned ablation model is a predictive model.

12. The system of claim 11, wherein the predictive model is a deep learning, neural network, or machine learning model.

13. The system of claim 11, wherein the predictive model is a non-linear regression algorithm.

14. The system of claim 1, wherein the processor is operable to execute a feasibility test for determining whether each said candidate path can allow a bronchoscope to reach the candidate POE based on a predefined path criteria selected from the group consisting of airway diameter, bronchoscope tip diameter, and bronchoscope bending angle.

15. The system of claim 14, wherein the processor is operable to execute a feasibility test for determining whether each said candidate path can access the target tissue from the airway without crossing vessels or other critical structures.

16. The system of claim 1, wherein the processor is programmed and operable to output an optimal ablation zone to maximize coverage of the target tissue, an optimal path to the target tissue, and generator parameters to provide said optimal ablation zone.

17. A bronchoscopic-based system for predicting an ablation zone for ablating a target tissue in a lung of a patient with an ablation applicator comprising:
   a storage for receiving image data of the lung of the patient including the target tissue to be ablated, and a first experimental data, wherein the first experimental data was generated by:
      ablating a first tissue according to a first set of ablation parameters,
      taking measurements of the first tissue subsequent to the ablating to obtain the first experimental data; and
   a processor programmed and operable to:

compute a plurality of candidate models based on the first experimental data;

compute, based on the image data of the lung, at least one candidate path for the ablation applicator to be advanced through the airway of the patient, to a candidate point of entry (POE), and through the airway wall to the target tissue; and determine a first learned ablation model based on the plurality of candidate models, wherein the first learned ablation model predicts ablation zone size for each said candidate path.

18. The system of claim 17, wherein the processor is further operable to compute a second learned ablation model based on a second experimental data, wherein the second experimental data was generated by ablating the first tissue or a second tissue according to a second set of ablation parameters; and to store the second learned ablation model.

19. The system of claim 18, wherein the processor is further operable to predict the ablation zone for ablating the target tissue in the patient based on applying at least one of the first learned ablation model and the second learned ablation model and at least one characteristic of the target tissue.

20. The system of claim 17 wherein the image data includes an annotated tumor.

21. The system of claim 17, wherein the processor is further operable to determine the first learned ablation model based on minimizing error between a predicted ablation zone and a measured ablation zone.

22. The system of claim 17, wherein the processor is further operable to determine the first learned ablation model based on cross validation, and wherein the cross validation is performed by (a) training using a plurality of subsets of the first experimental data as training data and (b) validating on a remaining part of the first experimental data.

23. The system of claim 17, wherein the ablation applicator is an electrosurgical device operable to deliver radiofrequency energy.

24. A bronchoscopic-based system for planning to ablate a target tissue in a lung of a patient with an ablation applicator comprising:

a storage for receiving image data of the lung of the patient including the target tissue to be ablated; and a processor programmed and operable to:

compute, based on the image data of the lung, at least one candidate path for the ablation applicator to be advanced through the airway of the patient to a candidate point of entry (POE), and from the POE to the target tissue;

create a learned ablation model based on past experimental data, and wherein the past experimental data includes measurements from ablation testing on sample tissue; and compute an ablation zone and ablation treatment parameters based on said learned ablation model to maximize ablation coverage of the target tissue for each said candidate path.

* * * * *